United States Patent [19]

Rosenberg et al.

[11] Patent Number: 4,942,162

[45] Date of Patent: Jul. 17, 1990

[54] TOPICAL TREATMENT OF SEBORRHEIC DERMATITIS WITH KETOCONAZOLE

[75] Inventors: E. William Rosenberg, Memphis; Patricia W. Belew-Noah, Germantown, both of Tenn.

[73] Assignee: University of Tennessee Research Corporation, Knoxville, Tenn.

[21] Appl. No.: 303,960

[22] Filed: Jan. 27, 1989

Related U.S. Application Data

[60] Continuation of Ser. No. 815,232, Dec. 31, 1985, abandoned, which is a division of Ser. No. 559,929, Dec. 9, 1983, Pat. No. 4,569,935, which is a continuation-in-part of Ser. No. 474,214, Mar. 17, 1983, Pat. No. 4,491,588, which is a continuation-in-part of Ser. No. 363,845, Mar. 31, 1982, abandoned.

[51] Int. Cl.$^5$ .................... A61K 31/50; A61K 31/495
[52] U.S. Cl. ....................................... 514/252; 514/864
[58] Field of Search ................................ 514/252, 864

[56] References Cited

U.S. PATENT DOCUMENTS

| | | | |
|---|---|---|---|
| 4,172,947 | 10/1979 | Warner et al. ...................... | 548/346 |
| 4,205,071 | 5/1980 | Durant et al. ....................... | 424/244 |
| 4,358,449 | 11/1982 | Heeres et al. ................... | 424/248.58 |

OTHER PUBLICATIONS

"Treatment of Pityriasis Capitis (Dandruff) with Econazole Nitrate", Acta Dermatovener (Stockholm), vol. 57, pp. 77–80 (1977)–Article discusses a dandruff treatment with Econazole Nitrate and discusses a casual relationship between fungal infestation and dermatological disorders.

"Activation of the Alternative Pathway of Complement by Malassezia Ovalis (Pityrosporum Ovale)", Mycopathologia, vol. 70.3, pp. 187–191 (1980)–Article discusses a mechanism for seborrheic dermatitis.

"Effect of Topical Applications of Heavy Suspensions of Killed Malassezia Ovalis on Rabbit Skin", Mycopathologia, vol. 72, pp. 147–154 (1980)–Article discusses experimentation leading to an explanation of human psoriasis.

"Sabouraud and Rivolta were Right–Seborrheic Dermatitis is Microbial", Cosmetics and Toiletries, Aug., 1981–Article discusses a mechanism for seborrheic dermatitis.

Chemical Abstracts, 97:84718d (1982).

Physicians Desk Reference (PDR), 34th ed., 1980, p. 1561.

*Primary Examiner*—Leonard Schenkman
*Attorney, Agent, or Firm*—Luedeka, Hodges & Neely

[57] ABSTRACT

A method is provided for treating psoriasis and seborrheic dermatitis in humans by topical application of an effective, lesion reducing amount of ketoconazole to affected areas.

3 Claims, No Drawings

TOPICAL TREATMENT OF SEBORRHEIC DERMATITIS WITH KETOCONAZOLE

This is a continuation of Ser. No. 815,232 filed Dec. 31, 1985 now abandoned, which is a division of Ser. No. 559,928, filed Dec. 9, 1983, now U.S. Pat. No. 4,569,935. Ser. No. 559,928 is a continuation-in-part of Ser. No. 474,214, filed Mar. 17, 1983, now U.S. Pat. No. 4,491,588 which is a continuation-in-part of Ser. No. 363,845 filed Mar. 31, 1982, now abandoned, all of which are assigned to the assignee of this invention.

The present invention relates to methods for the treatment of skin disorders of seborrheic dermatitis and psoriasis and more particularly relates to topical treatment of those disorders by topical application of imidazole antibiotics to affected areas.

Seborrheic dermatitis is a skin disorder characterized by lesions produced by an abnormal increase (>2X) in the production and shedding of epidermal cells from the skin, particularly in hairy areas, body folds, and in and behind the ears. Typically, the lesions have indefinite borders with an inflamed appearance and are covered by scales having a greasy appearance.

Psoriasis is a skin disorder also characterized by lesions produced by an even greater abnormal increase (10–20X) in the production of shedding of epidermal cells from the skin. Typically, psoriasis lesions, which are well-defined and have a pink or dull red color, are covered with silvery scales. In addition, capillaries in the skin in affected areas undergo swelling.

The causes of both seborrheic dermatitis and psoriasis are still in dispute and known topical treatments of the disorders are varied. One approach to the treatment of these disorders have involved the application of cytostatic agents to reduce the rate of cell growth and, thus, to decrease abnormal shedding of dead epidermal cells. Other treatments use corticosteroid products applied externally which have a general anti-inflammatory effect on all skin disorders including seborrheic dermatitis and psoriasis, but do not appreciably affect the rate of cell growth and shedding. Keratolytics have also been used to treat seborrheic dermatitis and psoriasis and act to dissolve and loosen the scales associated with the disorders, but such agents again do not prevent the rapid cell growth which produces the scales. Consequently, known treatments generally may produce some ostensible improvement but do not produce permanent clearing in most instances. In the case of some of these treatments, and particularly for those involving cytostatic compounds or corticosteroid products, there are often side effects which may prevent the use of those treatments for some patients.

Other agents used to treat seborrheic dermatitis and psoriasis include anthralins and coal tar derivatives which work in ways which are not entirely understood although it is generally believed that they have primarily cytostatic effects. These products also applied topically usually do not generally produce lasting and permanent improvement in seborrheic dermatitis and psoriasis.

It is accordingly an object of the present invention to provide a topical method for treating seborrheic dermatitis and psoriasis. It is another object to provide a safe method for treating seborrheic dermatitis and psoriasis which produces lasting improvement without dangerous side effects. Various other objects and advantages will be apparent from the following description.

Generally, in accordance with the present invention, seborrheic dermatitis and psoriasis in humans are effectively treated by a topical application of an imidazole antibiotic to affected areas, in an effective, lesion reducing amount. While various imidazole antibiotics may be employed, the preferred compounds are selected from the group consisting of ketoconazole [cis-1-acetyl-4-[4-[[2-(2,4-dichlorophenyl)-2(1H-imidazole-1-ylmethyl)-1,3-dioxolan-4-yl]methoxy]phenyl]piperazine and clotrimazole[1-(o-Chloro-a,a-diphenylbenzyl)imidazole].

The topical application of the imidazole antibiotics is performed by applying a dilute solution of the imidazole antibiotic to affected areas. An inert lotion or cream containing the imidazole antibiotic in a 1–5% concentration by weight is preferred. The inert lotion or cream may be any known inert vehicle suitable for topical applications.

A ketoconazole cream may be prepared by dissolving the ketoconazole in water whose pH has been adjusted to pH 4 by the dropwise addition of 0.1N HCl to produce a ketoconazole solution. This solution is mixed with an emulsion base, i.e. polyethylene glycol, U.S. P., to produce an active cream with the desired concentration. A 2% ketoconazole cream is particularly effective.

A clotrimazole cream may be prepared similarly and is also particularly effective in about a 2% concentration. Topical application is preferably performed twice daily but may be applied more or less often as needed.

Imidazole antibiotics applied topically in humans have the main effect of controlling or inhibiting the growth of various yeasts, fungi, or bacteria and the topical use of the compounds for treating seborrheic dermatitis and psoriasis presents an effective treatment method without the side effects associated with known treatment methods.

The invention will be better understood from the following examples which are given by way of illustration and not by way of limitation.

EXAMPLE I

An 18 year old female had scalp psoriasis of the frontal hairline and occipital area. After four months of topical application of a 2% ketoconazole cream applied twice daily, the patient's scalp was completely clear of psoriasis.

EXAMPLE II

A 44 year old female had psoriasis of the frontal hairline, ears, and face with severe scaling and redness. Topical application of 2% ketoconazole cream applied twice daily for nine months produced clearing with mild scaling and redness remaining only in the post auricular area.

EXAMPLE III

A 26 year old female has had seborrheic dermatitis of the scalp, hairline and face for two years. Topical application of 2% ketoconazole cream applied twice daily for two months resulted in substantial clearing with only two 2 cm×2 cm areas having mild scaling.

EXAMPLE IV

A 33 year old female has had severe seborrheic dermatitis of the scalp, hairline, and ear area for 15 years. Topical application of 2% ketoconazole cream applied twice daily for two months produced substantial clearing with mild scaling remaining only in the external ear canal.

EXAMPLE V

A 31 year old male had chronic seborrheic dermatitis of the forehead, brow, and nasolabial fold. Topical application of 2% clotramazole cream applied twice daily for two months resulted in substantially complete clearing.

The topical use of imidazole antibiotics for the treatment of seborrheic dermatitis or psoriasis according to the present invention merely requires twice daily application of a cream or lotion to the affected areas for a period of two months to nine months. Generally, no special precautions are required other than the general precautions which accompany the topical application of antibiotics to the skin. Moreover, no special laboratory testing of patients is required. Evaluation of the effectiveness of the medication is by simple examination of the patient and by changes in the amounts of itching present.

Topical application of imidazole antibiotics on a twice daily basis generally produces beneficial effects on seborrheic dermatitis and psoriasis when applied over a period of time. As with any treatment, there are some patients who do not respond as well as others. However, in the case of treatment with ketoconazole, the treatment has been highly successful in substantially every case with complete or substantially complete clearing of seborrheic dermatitis or psoriasis being effected and with clearing lasting for a prolonged period after treatment.

While a preferred embodiments have been described in the foregoing detailed description, it will be recognized that there is no intent to limit the invention by such disclosure, but rather it is intended to cover all modifications and variations falling within the spirit and scope of the invention as defined in the appended claims.

What is claimed is:

1. A method of treating seborrheic dermatitis in humans by topical application of an effective, lesion reducing, amount of ketoconazole to affected areas.

2. The method of claim 1 wherein said ketoconazole is applied in a water based cream having a 1–5% concentration of said ketoconazole.

3. The method of claim 2 wherein said ketoconazole is applied twice daily.

* * * * *